(12) United States Patent
Joseph et al.

(10) Patent No.: US 11,237,151 B2
(45) Date of Patent: Feb. 1, 2022

(54) INTERCHANGEABLE TEST ELEMENT RETAINERS

(71) Applicant: Roche Diabetes Care, Inc., Indianapolis, IN (US)

(72) Inventors: Abner Joseph, Carmel, IN (US); Mark Offenbacher, Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 16/846,805

(22) Filed: Apr. 13, 2020

(65) Prior Publication Data

US 2020/0240976 A1 Jul. 30, 2020

Related U.S. Application Data

(62) Division of application No. 15/314,580, filed as application No. PCT/US2015/033521 on Jun. 1, 2015, now Pat. No. 10,663,451.
(Continued)

(51) Int. Cl.
*G01N 33/487* (2006.01)
*B65D 25/10* (2006.01)
(Continued)

(52) U.S. Cl.
CPC ....... *G01N 33/48778* (2013.01); *B65D 25/10* (2013.01); *B65D 43/16* (2013.01); *B65D 53/02* (2013.01); *G01N 33/48757* (2013.01)

(58) Field of Classification Search
CPC ....... G01N 33/48778; G01N 33/48757; G01N 33/48745; B65D 25/10; B65D 25/02;
(Continued)

(56) References Cited

U.S. PATENT DOCUMENTS 1,450,674 A * 4/1923 Marston ............... A45C 7/0031
220/8
2,727,547 A * 12/1955 Edward .................. A45C 11/22
220/555
(Continued)

FOREIGN PATENT DOCUMENTS

| CN | 101266241 A | 9/2008 |
|---|---|---|
| JP | S5071371 U | 6/1974 |
| WO | 199639346 A1 | 12/1996 |

*Primary Examiner* — Steven A. Reynolds
*Assistant Examiner* — Javier A Pagan
(74) *Attorney, Agent, or Firm* — Stinson LLP (57) ABSTRACT

Interchangeable inserts are provided for a storage container configured to receive a plurality of vertically oriented items, where the inserts include a body having a base, an upper surface having an upper opening, and an upstanding tubular sidewall extending between the base and the upper surface. The base and the tubular sidewall together define an interior space of the insert. The tubular sidewall has an inner surface and an outer surface, where a pair of resilient securing tabs extend laterally from the outer surface of the tubular sidewall. The securing tabs frictionally engage the storage container for releasably coupling the insert to the storage container. Further, the insert has a first vent opening extending through the tubular sidewall through which air can enter the interior space of the body.

9 Claims, 7 Drawing Sheets

Related U.S. Application Data (60) Provisional application No. 62/008,152, filed on Jun. 5, 2014.

(51) Int. Cl.
  B65D 43/16 (2006.01)
  B65D 53/02 (2006.01)

(58) Field of Classification Search
  CPC ........ B65D 25/00; B65D 43/16; B65D 43/14; B65D 53/02
  See application file for complete search history.

(56) References Cited

U.S. PATENT DOCUMENTS

| | | | | |
|---|---|---|---|---|
| 3,918,920 A | * | 11/1975 | Barber | B01L 9/06 422/560 |
| 7,670,562 B2 | * | 3/2010 | Sacherer | B01L 9/527 422/562 |
| 8,394,346 B2 | * | 3/2013 | Emin | C01G 56/001 423/8 |
| 9,052,305 B2 | * | 6/2015 | Newman | G01N 33/48757 |
| 2006/0182656 A1 | * | 8/2006 | Funke | G01N 33/48757 422/400 |
| 2007/0196240 A1 | * | 8/2007 | Boozer | G01N 33/48778 422/400 |
| 2011/0127269 A1 | * | 6/2011 | Bucholtz | B65D 43/162 220/378 |
| 2011/0174644 A1 | * | 7/2011 | Chan | B65D 43/16 206/305 |
| 2013/0134159 A1 | * | 5/2013 | Chan | B01L 9/52 220/23.83 |
| 2014/0014677 A1 | * | 1/2014 | Chan | B65D 83/0829 221/232 |
| 2016/0001927 A1 | * | 1/2016 | Lucas, Jr. | B65D 83/12 206/204 |
| 2017/0166387 A1 | * | 6/2017 | Yao | B65D 83/0829 |

* cited by examiner

INTERCHANGEABLE TEST ELEMENT RETAINERS

CROSS-REFERENCE TO RELATED APPLICATIONS

This application is a divisional of U.S. patent application Ser. No. 15/314,580, filed Nov. 29, 2016, which claims priority to and the benefit of International Publication Number WO2015/187551, filed on Jun. 1, 2015, which claims priority to and the benefit of U.S. Provisional Patent Application No. 62/008,152, filed on Jun. 5, 2014, both of which are-incorporated herein by reference as if set forth in their entireties.

TECHNICAL FIELD

This patent application relates generally to engineering and medical diagnostics, and more particularly, it relates to interchangeable inserts for vertically oriented test elements within a storage container.

BACKGROUND

Systems, apparatuses and methods for assaying biological fluids, as well as test elements for use therein, are well known. Typically, test elements are stored in a storage container that is distinct from a test meter that analyzes a biological fluid sample. In some systems, a test element is first removed from the storage container, a biological fluid sample then is deposited onto a region of the test element, and the test element is inserted into the test meter for analysis of an analyte of interest. After the analysis is complete, the test element is removed from the test meter and disposed.

Some known storage containers are designed and built to store multiple test elements of a specific number and a single size, or use an interchangeable insert for different test elements, both of which present disadvantages. For example, storage containers designed and built to store multiple test elements of a specific number and a single size may lead to increased container manufacturing and inventory costs. Additionally, some known interchangeable inserts for such storage containers are prone to cumbersome loading of the insert or dislodging of the insert if the storage container is dropped or otherwise knocked around. Dislodging of the insert can result in inadvertent or accidental spillage of the test elements that may lead to contamination and unreliability thereof. Furthermore, a partially dislodged insert may adversely affect the perceived quality of the interchangeable insert storage container by an end user.

With some known storage containers, as a quantity of the test elements are used and disposed by the user, the remaining test elements may slide further into the insert, which does not allow for easy access and removal of a single test element by the user. In view of the ramifications of accurate recording, reporting and analyzing of biological fluid samples, improvements in storage containers for storing and distributing test elements used to analyze biological fluid samples are desired.

BRIEF SUMMARY

Briefly, an inventive concept described herein includes providing interchangeable inserts for test elements that have improved insert retention within a storage container, as well as improved vertically oriented test element retention. The inventive concept is achieved by providing the inserts with resilient securing tabs that can frictionally engage the storage container for releasably coupling the insert to the storage container. Additionally, the inserts can include retainer elements for assisting in maintaining a vertical orientation of test elements. The inventive concept therefore is embodied in exemplary systems, apparatuses, devices, storage containers and interchangeable inserts as described herein.

For example, inserts are provided for a storage container configured to receive a plurality of vertically oriented items. The inserts include a body having a base, an upper surface having an upper opening, and an upstanding tubular sidewall extending between the base and the upper surface. The base and the tubular sidewall together define an interior space. The tubular sidewall includes an inner surface and an outer surface. The inserts also include a pair of resilient securing tabs extending laterally from the outer surface of the tubular sidewall. The securing tabs are configured to frictionally engage the storage container for releasably coupling the insert to the storage container. In addition, the inserts can include a first vent opening extending through the tubular sidewall through which air can enter the interior space of the body.

Additionally or alternatively, inserts are provided for a storage container configured to receive a plurality of vertically oriented items. The inserts include a first side portion and a second side portion hingedly coupled together. Each one of the first side portion and the second side portion has a base, an upper surface having an upper opening, and an upstanding tubular sidewall extending between the base and the upper surface, where the tubular sidewall has an inner surface and an outer surface. Each one of the first side portion and the second side portion has a lip coupled to the outer surface of the tubular sidewall, the lip being spaced away from the upper surface. The first side portion and a second side portion are moveable between a closed configuration where the first side portion and the second side portion are in face-to-face contact, and an open configuration where the first side portion and the second side portion are spaced apart. The inserts also include a catch member coupled to one of the first side portion and the second side portion. The catch member extends between an upper surface and the lip, and defines a catch opening. The inserts further include a latch member coupled to the outer surface of the tubular sidewall of the other one of the first side portion and the second side portion. In addition, the inserts have a living hinge coupled between the first side portion and the second side portion to enable the first side portion and the second side portion to be rotated into face-to-face contact. The latch member extends through the catch opening and engages the catch member when an insert is in the closed configuration. As above, the inserts also can include a pair of resilient securing tabs as described above for frictionally retaining the insert in a storage container.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Corresponding reference characters indicate corresponding parts throughout the several views of the drawings.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

Overview

The systems, apparatuses, devices, storage containers and interchangeable inserts now will be described more fully hereinafter with reference to the accompanying drawings, in which some, but not all embodiments of the inventive concept are shown. Indeed, the systems, apparatuses, devices, storage containers and interchangeable inserts may be embodied in many different forms and should not be construed as limited to the embodiments set forth herein; rather, these embodiments are provided so that this disclosure will satisfy applicable legal requirements.

Likewise, many modifications and other embodiments of the systems, apparatuses, devices, storage containers and interchangeable inserts described herein will come to mind to one of skill in the art to which the disclosure pertains having the benefit of the teachings presented in the foregoing descriptions and the associated drawings. Therefore, it is to be understood that the systems, apparatuses, devices, storage containers and interchangeable inserts are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the systems, apparatuses, devices, storage containers and interchangeable inserts, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Furthermore, approximating language, as used herein and in the claims, may be applied to modify any quantitative representation that could permissibly vary without resulting in a change in the basic function to which it is related. Accordingly, a value modified by a term or terms, such as "about," "approximately" and "substantially" is not to be limited to the precise value specified. In at least some instances, the approximating language may correspond to the precision of an instrument for measuring the value. Likewise, range limitations may be combined or interchanged; such ranges are identified and include all the sub-ranges contained therein unless context or language indicates otherwise.

For example, as used herein, "about" means within a statistically meaningful range of a value or values such as, for example, a stated concentration, length, width, height, weight, pH, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The systems, apparatuses, devices, storage containers and interchangeable inserts are useful in a variety of applications. For example, the interchangeable inserts can be used to hold a plurality of vertically oriented test elements. Because the inserts frictionally engage a surface of a storage container, they can be readily removed when no test elements remain. Advantageously, inserts having either the same or different numbers of test elements, as well as the same or different sized/shaped test elements, can be used interchangeably.

Storage Containers and Interchangeable Inserts

Figure 1:
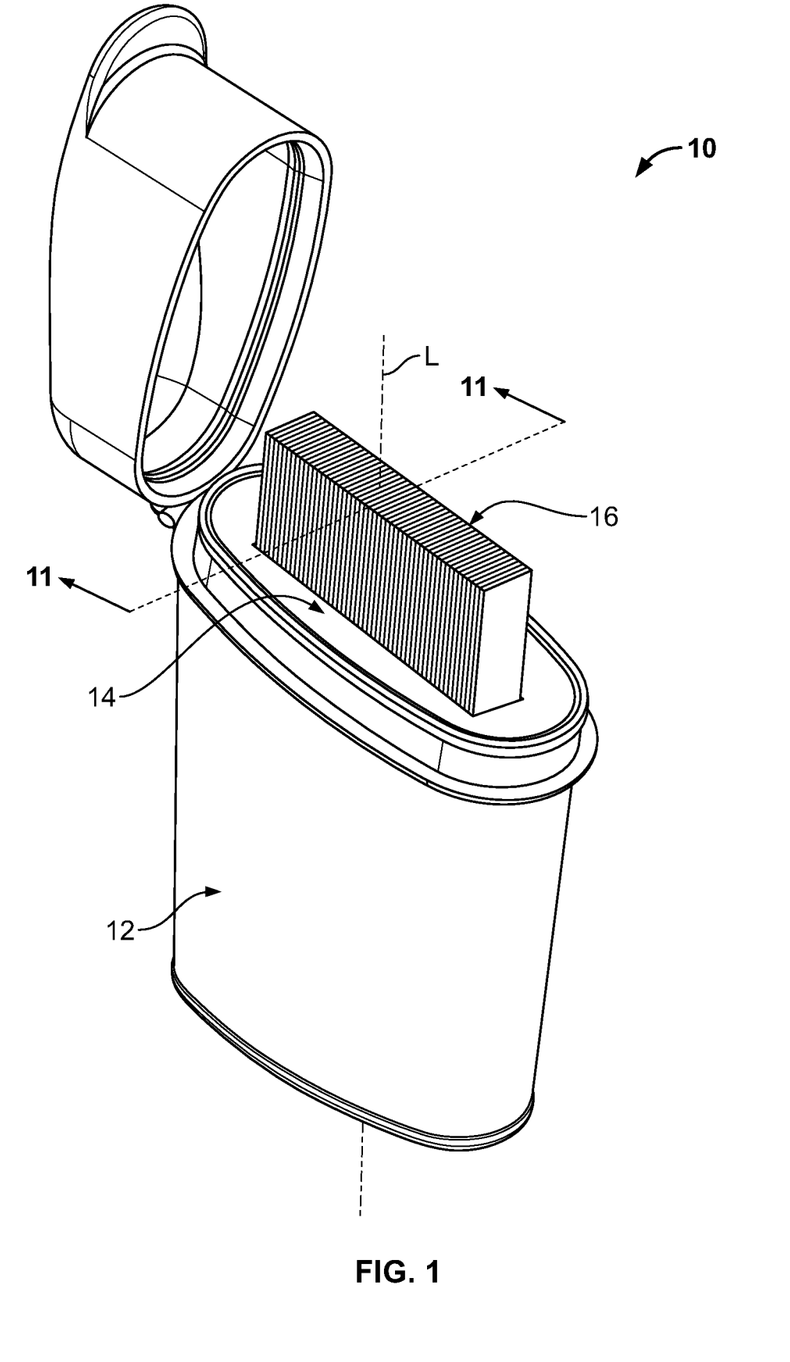
FIG. 1 is a perspective view of an exemplary storage container.
Figure 2:
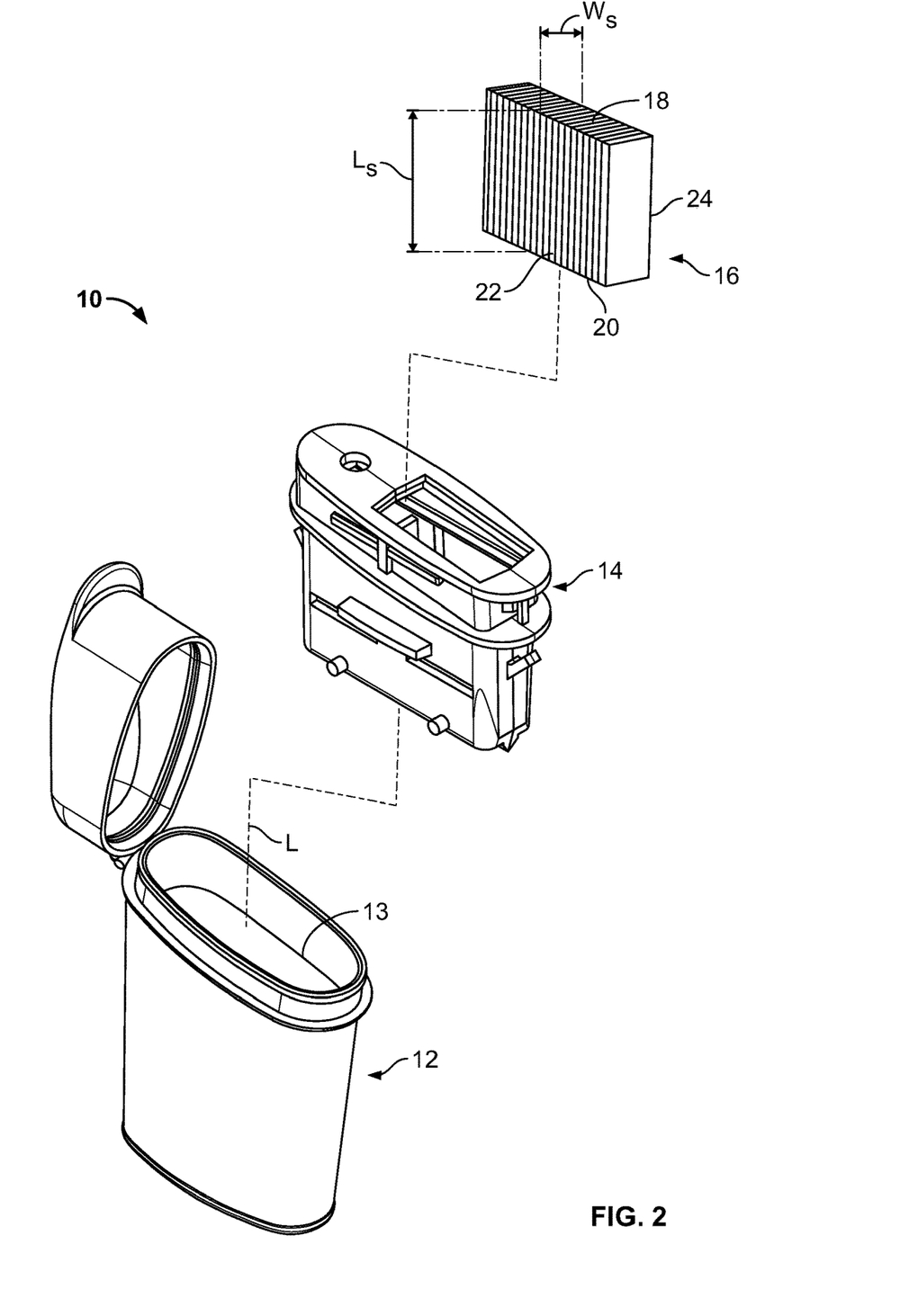
FIG. 2 is an exploded perspective view of the storage container shown in FIG. 1.

FIG. 1 is a perspective view of an exemplary storage container 10. FIG. 2 is an exploded perspective view of the storage container 10 shown in FIG. 1. In the exemplary embodiment, the storage container 10 is configured to retain a plurality of items 16 such as, for example, test elements. The storage container 10 extends along a central longitudinal axis L and includes a housing 12 and an interchangeable insert 14 positioned within an interior volume of the housing 12. The insert 14 is configured to retain the test elements 16 therein. In the exemplary embodiment, the housing 12 and the insert 14 each can be fabricated from a polymeric or plastic material including, for example, polypropylene or polyethylene. Alternatively, the housing 12 and the insert 14 may be fabricated from any other suitable materials that enable the housing 12 and the insert 14 to function as described herein including, but not limited to, composite or metallic materials. It also is understood that the housing 12 and the insert 14 can be made in any desired color or colors, and may be transparent, translucent, or opaque.

Optionally, a desiccant 13 can be used in association with the storage container 10 (and/or the insert 14) to facilitate reducing humidity or moisture within the interior region of the storage container 10. Excess humidity or moisture within the storage container 10 can adversely affect the integrity of the test elements 16. More specifically, the desiccant 13 may be incorporated directly into the housing 12 of the storage container 10 or may be provided anywhere within an interior space of the housing 12.

In some instances, one or more portions of the housing 12 and/or the insert 14 may be partially or entirely formed from an injection moldable desiccant material. For example, one or more of the walls of the housing 12 and/or the insert 14 may be formed from a desiccant-entrained polymer material, although other suitable configurations and materials are contemplated. In other instances, desiccant 13 can be a separate component placed within the interior space 36 of the housing 12 such as, for example, a desiccant packet, a desiccant canister, a desiccant pellet, a particulate desiccant material, or other elements or structures including a desiccant material. Alternatively or additionally, other types and compositions of desiccant are contemplated for use with the storage container 10 including, but not limited to, porous paper, cellulosic fiber, a desiccant entrained polymer, porous plastic, molecular sieves, silica gels, clays, starches, calcium sulfate, calcium oxides, calcium chloride, and the like, and combinations thereof.

In the exemplary embodiment, the test elements 16 have a substantially rectangular shape and include an end edge 18, and an opposite end edge 20 spaced apart from end edge 18 a length Ls. In addition, each of the test elements 16 include a side edge 22, and an opposite side edge 24 spaced apart from side edge 22 a width Ws. Alternatively, the test elements 16 may have any other suitable shape and configuration that enables storage container 10 to function as described herein. In the exemplary embodiment, the test elements 16 are biosensor test strips configured to measure glucose levels in a body fluid sample such as blood when used in connection with a blood glucose meter (not shown) or other suitable measurement device or system. Alternatively, the test elements 16 may be any type or configuration of test element that enables the storage container 10 to function as described herein. Additionally, the storage container 10 may be used to store other types of analytical elements, diagnostic devices, or other medical or pharmacological devices.

In the exemplary embodiment, the interchangeable insert 14 is releasably coupled to the housing 12. It is understood that various types, sizes, and configurations of the insert 14 thus may be used interchangeably with the housing 12 to accommodate a variety of types, sizes, and configurations of the test elements 16. One advantage of the interchangeable configuration of storage container 10 and insert 14 is that manufacturing costs and inventory levels can be reduced since one type or size of the housing 12 may be used in association with several types or sizes of the insert 14. The insert 14 can be provided as a disposable component that is discarded when the insert 14 no longer contains any of the test elements 16. A new insert 14 containing a new set of test elements 16 may be positioned within the housing 12. Alternatively, the insert 14 can be refilled with a new set of test elements 16.

Figure 3:
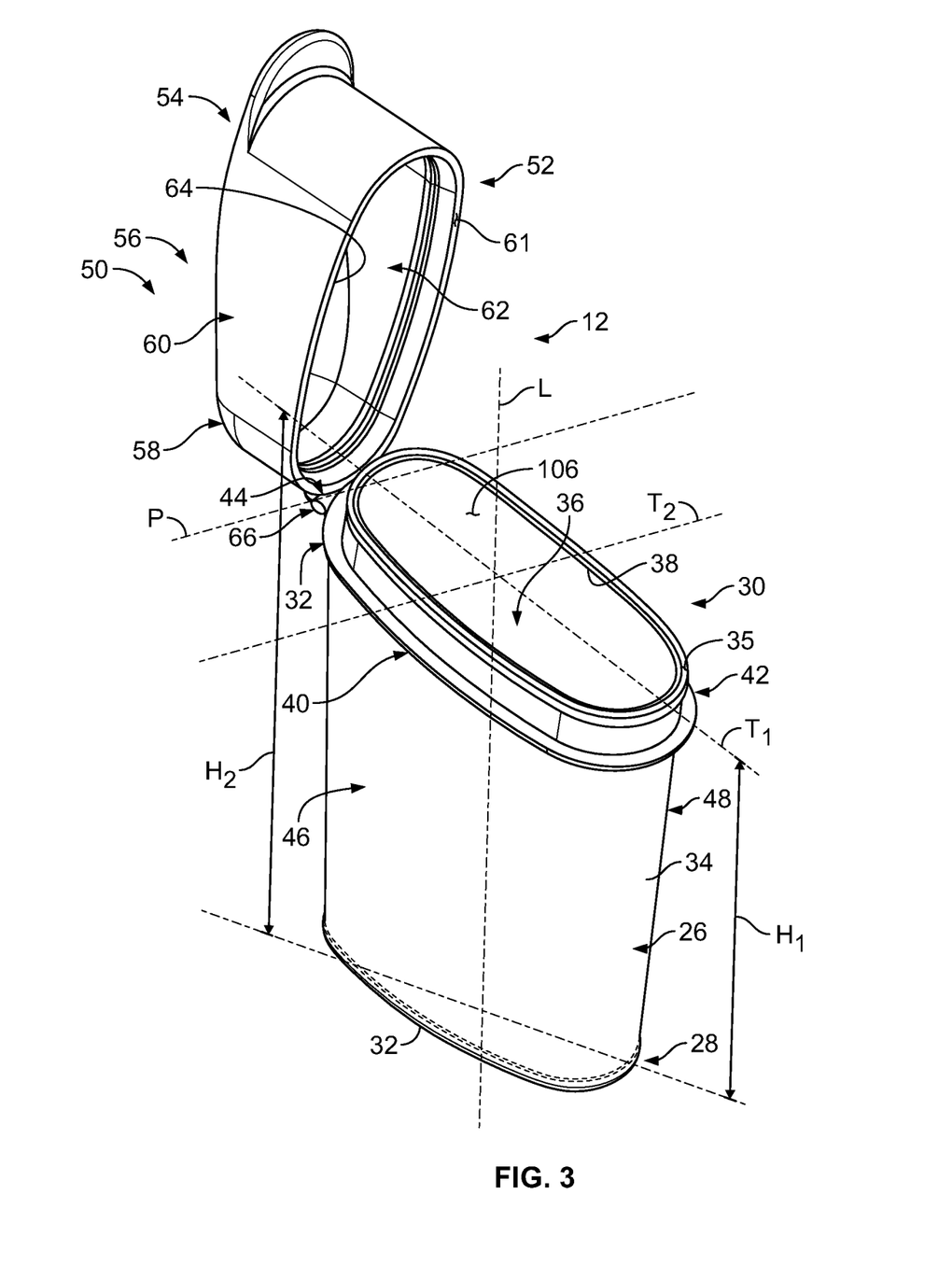
FIG. 3 is a perspective view of a housing that can be used with the storage container shown in FIG. 1.

FIG. 3 is a perspective view of the housing 12 that can be used with the storage container 10 shown in FIG. 1. The housing 12 has a height extending along the longitudinal axis L and generally includes a body 26 and a removable cap 50 (broadly, a closure) rotatably attached to the body 26. The body 26 has a lower end portion 28 and an upper end portion 30. The body 26 includes a substantially planar base or bottom wall 32 adjacent the lower end portion 28. A tubular sidewall 34 extends upward along the longitudinal axis L from the bottom wall 32 toward the upper end portion 30, defining a top rim 35. The bottom wall 32 and the sidewall 34 together define a tubular configuration having an upper opening 38 and an interior space 36. In one suitable embodiment, the body 26 also includes a shoulder or lip 40 extending substantially perpendicularly outward from the sidewall 34. The lip 40 is located generally adjacent the upper opening 38 and is configured for engagement with the cap 50. In the exemplary embodiment, the cap 50 is configured to close off the upper opening 38.

In some instances, the body 26 may include one or more sealing members (not shown) such as, for example, a gasket, an O-ring, or a sealable foil positioned on or adjacent the top rim 35, the lip 40, or along the bottom portion of the cap 50 to provide sealing engagement between the body 26 and the cap 50. The sealing members may establish a seal between the body 26 and the cap 50 to prevent moisture or contaminants from entering the interior region of the storage container 10, or to provide a seal to isolate the test elements 16 from the external environment. The sealing members (not shown) may be fabricated from materials including, but not limited to, rubber, plastic, polymeric, synthetic, or metallic material.

In the exemplary embodiment, the body 26 is substantially elliptically shaped and includes an elongate dimension (i.e., a length) extending along a major transverse axis T1 from a front portion 42 to a rear portion 44 of the housing 12. The body 26 also includes a transverse dimension (i.e., a width) extending along a minor transverse axis T2 from a first side portion 46 to an opposite second side portion 48 of the body 26. In the exemplary embodiment, the major and minor transverse axes T1 and T2 intersect one another at the central longitudinal axis L. Alternatively, the body 26 may be fabricated in other shapes including, but not limited to, a rectangular cross section, a curvilinear cross section, a polygonal cross section, a circular cross section, a square cross section, or any other suitable cross-sectional shape that enables housing 12 to function as described herein. Additionally, the body 26 has a first height H1 adjacent the front portion 42 and a second height H2 adjacent the rear portion 44 to thereby provide the body 26 of the housing 12 with a varying height dimension. Alternatively, the body 26 may be fabricated with a substantially uniform height.

In the exemplary embodiment, the removable cap 50 has a lower end portion 52 and an upper end portion 54. The cap 50 has a substantially planar upper wall 56 adjacent the upper end portion 54. A tubular sidewall 60 extends from the upper wall 56 toward the lower end portion 52, defining a bottom rim 61. The upper wall 56 and the sidewall 60 together define a tubular configuration having an interior space 62 and a lower cap opening 64. In one suitable embodiment, the cap 50 may include an inner shoulder or lip (not shown) extending annularly about an inner surface of the sidewall 60 adjacent the lower cap opening 64 for engagement with the top rim 35 of the body 26. In the exemplary embodiment, the cap 50 is configured to close off the upper opening 38 of the body 26.

In some instances, the cap 50 may include one or more sealing members (not shown) such as, for example, a gasket, an O-ring, or a sealable foil positioned on or adjacent the bottom rim 61 (or the inner shoulder or lip) to provide sealing engagement between the body 26 and the cap 50. The sealing members may be fabricated from materials including, but not limited to, rubber, plastic, polymeric, synthetic, metallic material, or combinations thereof.

In the exemplary embodiment, the cap 50 is suitably positionable between a closed position (not shown) and an open position (FIG. 3) in which the interior space 36 of the body 26 is accessible. More particularly, the exemplary cap 50 is hinged to the rear portion 44 of the body 26, and in particular, to the lip 40 for hinged motion relative thereto, and more suitable relative to the body 26, between the closed and open positions of the cap 50. For example, as seen in FIG. 3, the cap 50 may be hinged to the lip 40 in the manner of a "living hinge" 66 in which the cap 50 is formed (e.g., molded) integrally with the lip 40 along a thinned or scored connecting web that is sufficiently flexible to allow hinged motion of the lid relative to the lip 40. It is understood, though, that the cap 50 may be formed separate from the body 26 and mechanically hinged thereto by a suitable hinge mechanism (not shown) without departing from the scope of this invention. The hinge 66 enables the cap 50 to pivot about a pivot axis P between open and closed positions relative to the body 26.

In the exemplary embodiment, the pivot axis P is arranged generally parallel with the minor transverse axis T2 of the body 26. Alternatively, the pivot axis P may be arranged generally parallel with the major transverse axis T1 of the body 26, or may be arranged at an oblique angle relative to the major or minor transverse axes T1 and T2. It is contemplated that the cap 50 can be attached to the body 26 by other suitable attachment techniques or separate from the body 26 until fully engaged to the body 26 in the closed position. When the cap 50 is in the open position (FIG. 3), the upper opening 38 is unobstructed to provide access to the test elements 16 contained therein (FIG. 1). When the cap 50 is in the closed position (not shown), the upper opening 38 is covered or closed off to protect and retain the test elements 16 within the storage container 10 or to prevent moisture or contaminants from entering the storage container 10.

In the exemplary embodiment, the cap 50 is substantially elliptically shaped and substantially corresponds to the elliptical shape of the body 26. Alternatively, the cap 50 may be fabricated in other shapes including, but not limited to, a rectangular cross section, a curvilinear cross section, a polygonal cross section, a circular cross section, a square cross section, or any other suitable cross-sectional shape that enables the housing 12 to function as described herein. The cap 50 has a first height adjacent a front portion 53 and a second height adjacent a rear portion 58, wherein the second height is less than the first height to provide the cap 50 with a varying cap height. Alternatively, the cap 50 may be fabricated with a substantially uniform height.

In the exemplary embodiment, when the cap 50 is in the closed position (not shown) and engaged with the body 26, the varying height of the cap 50 cooperates with the varying height of the body 26 to provide the housing 12 with a substantially uniform overall height. In some instances, the body 26 and the cap 50 are provided with engagement features (not shown) configured to cooperate with one another to releasably couple the cap 50 in the closed position (not shown). For example, the body 26 and the cap 50 may include detent features, interlocking features, snap features, or fastening features (not shown) that releasably couple the cap 50 in the closed position (not shown) relative to the body 26. In other instances, the cap 50 can be configured to engage the body 26 via a threaded arrangement, a twist lock arrangement, a bayonet lock arrangement, a friction fit arrangement, or other suitable engagement arrangements (not shown). In still other instances, the cap 50 may be provided with a passage (not shown) extending therethrough and communicating with the interior space 36 of the body 26, and with a closing member (not shown) cooperating with the passage such that one or more of the test elements 16 can be removed from the interior space 36 without having to disengage the cap 50 from the body 26. The closing member (not shown) may be in the form of a plug, valve or other suitable closeable access device (not shown).

Figure 4:
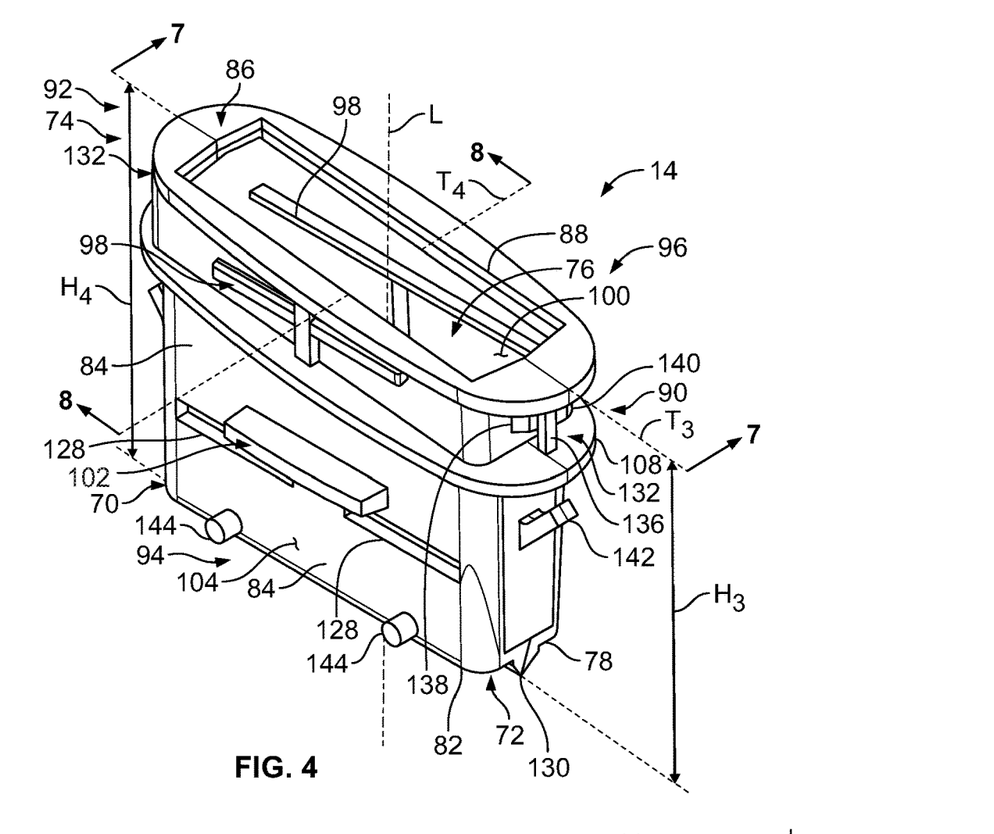
FIG. 4 is a perspective view of an interchangeable insert that can be used with the storage container shown in FIG. 1.
Figure 5:
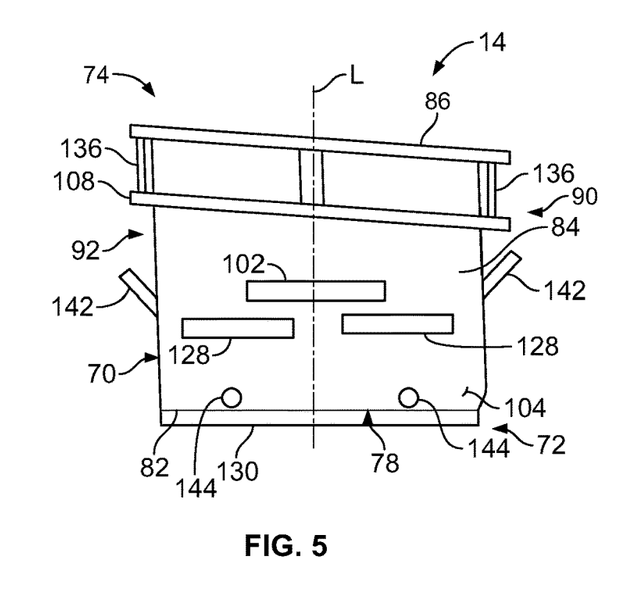
FIG. 5 is a side view of the insert shown in FIG. 4.
Figure 6:
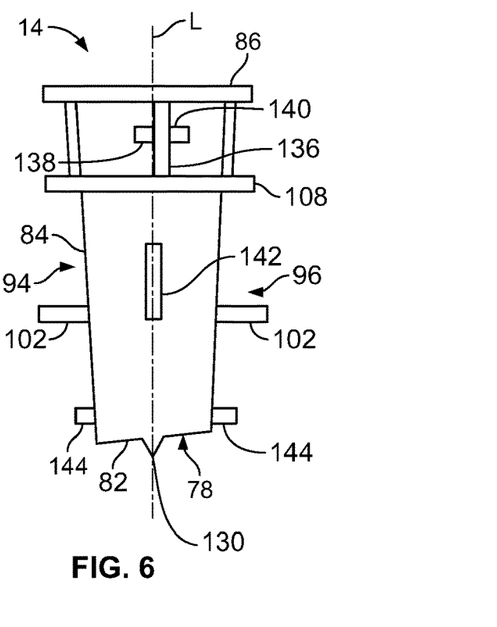
FIG. 6 is an end view of the insert shown in FIG. 4.
Figure 7:
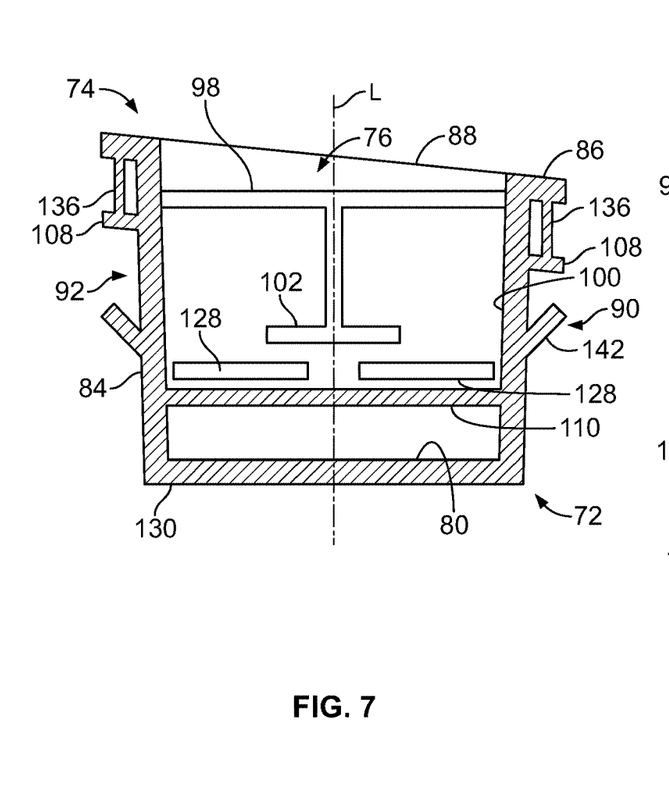
FIG. 7 is a cross sectional view of the insert shown in FIG. 4, taken along line 7-7 in FIG. 4.
Figure 8:
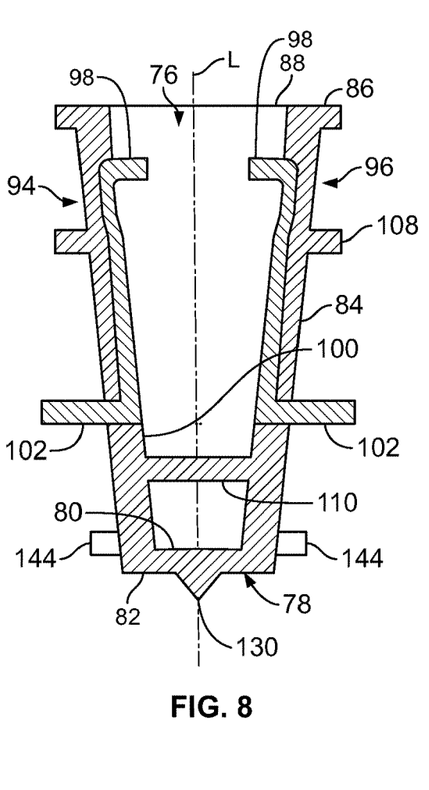
FIG. 8 is a cross sectional view of the insert shown in FIG. 4, as taken along line 8-8 in FIG. 4.

FIG. 4 is a perspective view of an exemplary interchangeable insert 14 that can be used with the storage container 10 shown in FIG. 1. FIG. 5 is a side view of the insert 14, and FIG. 6 is an end view of the insert 14. Further, FIG. 7 is a cross sectional view of the insert 14 taken along section line 7-7, and FIG. 8 is a cross sectional view of the insert 14 taken along section line 8-8, each section line shown in FIG. 4. With reference to FIGS. 4-8, in the exemplary embodiment, insert 14 is configured for interchangeable engagement with the housing 12. The insert 14 includes a main body 70 having a lower end portion 72 and an upper end portion 74. The main body 70 includes an interior space 76 configured to receive and retain one or more test elements 16 (see, FIG. 1) therein.

The main body 70 further includes a substantially planar base or bottom wall 78 having an inner surface 80 and an outer surface 82. Positioned within the interior space 76 and spaced upward and substantially parallel to bottom wall 78 is a floor panel 110 configured for engaging the end edge 20 of the test elements 16. Floor panel 110 may be spaced apart from bottom wall 78 at various predefined distances within interior space 76 based on the length Ls of test elements 16 to position test elements 16 for relatively easy removal from the insert 14. It is contemplated that the floor panel 110 may be omitted from the main body 70 and that the bottom wall 78 may function to engage the end edge 20 of the test elements 16.

In the exemplary embodiment, the main body 70 also includes an upstanding tubular sidewall 84 that extends substantially axially along the longitudinal axis L from the bottom wall 78 toward the upper end portion 74, terminating at a top or upper surface 86. The bottom wall 78 and the sidewall 84 together define a tubular configuration having the interior space 76 and an upper opening 88 at the upper surface 86. In the exemplary embodiment, the shape of the upper opening 88 corresponds substantially to the shape of the tubular sidewall 84, having a generally rectangular tubular shape having its inner edge coterminous with an inner surface 100 of the tubular sidewall 84. Alternatively, the upper opening 88 can have any shape that enables the insert 14 to function as described herein.

In the exemplary embodiment, the upper surface 86 of the insert 14 includes an outward extending annular flange having a periphery that is substantially elliptically shaped and substantially corresponds to the elliptical shape of the body 26 of the housing 12. The insert 14 includes an elongate dimension (i.e., a length) extending along a major transverse axis T3 from a front portion 90 to a rear portion 92 of the insert 14. The insert 14 also includes a transverse dimension (i.e., a width) extending along a minor transverse axis T4 from a first side portion 94 to an opposite second side portion 96 of the insert 14. In the exemplary embodiment, the elongate dimension and the transverse dimension are sized such that insert 14 can be interchangeably inserted into the interior space 36 of the body 26.

As shown in FIG. 6, the first side portion 94 and the second side portion 96 are substantially symmetrical with respect to the longitudinal axis L, which, when viewed from the end, is substantially centered on insert 14. Alternatively, insert 14 may include features and/or elements that are not symmetrical with respect to each other. The terms top, bottom, front, rear, left, and right are used herein only for convenience to indicate relative positional relationships. In one suitable embodiment, the first side portion 94 and the second side portion 96 are separate components hingedly coupled together.

Further, in the exemplary embodiment, the major and minor transverse axes T3 and T4 of the substantially elliptically shaped insert 14 intersect one another at the central longitudinal axis L. Alternatively, the insert 14 may be fabricated in other shapes including, but not limited to, a rectangular cross section, a curvilinear cross section, a polygonal cross section, a circular cross section, a square cross section, or any other suitable symmetrical cross-sectional shape that enables insert 14 to function as described herein.

In the exemplary embodiment, the insert 14 includes a substantially elliptically shaped lip 108 spaced from and substantially parallel to the upper surface 86. The lip 108 is sized to substantially correspond to the elliptical shape of the upper surface 86 and is configured to fit into the interior space 36 of the housing 12 to facilitate positioning the insert 14 properly within the housing.

Furthermore, in the exemplary embodiment, the insert 14 has a first height H3 adjacent the front portion 90 and a second height H4 adjacent the rear portion 92 of the insert 14 to thereby provide the insert 14 with a varying height dimension. Moreover, the insert 14 may be provided with a height profile that generally corresponds to the height profile of the housing 12 where the upper surface 86 is configured to be substantially flush with the top rim 35 of the body 26 of the housing 12 (see, FIG. 1). Alternatively, the upper surface 86 may be configured to be recessed below or elevated above the top rim 35 of the body 26, or the insert 14 may be fabricated with a substantially uniform height profile that does not correspond with the height profile of the body 26 of the housing 12.

In the exemplary embodiment, the main body 70 of the insert 14 includes a pair of resilient retainer elements 98 offset from upper surface 86 and within interior space 76. Alternatively, the main body 70 may include any number of retainer elements 98 that enable insert 14 to function as described herein. In the exemplary embodiment, the retainer elements 98 extend inwardly from the inner surface 100 of the tubular sidewall 84 and laterally into the interior space 76. More specifically, the retainer elements 98 extend inwardly from the inner surface 100 corresponding to the first side portion 94 and the second side portion 96 of the insert 14. In the exemplary embodiment, the retainer elements 98 extend substantially the entire length of interior space 76, from the front portion 90 to the rear portion 92 of the insert 14. Alternatively, the retainer elements 98 may extend from the front portion 90 toward the rear portion 92 any length that enables insert 14 to function as described herein.

The retainer elements 98 are formed substantially parallel to the bottom wall 78. However, it is understood, that the retainer elements 98 can be formed at an angle relative to the bottom wall 78 (e.g., retainer elements 98 can be formed substantially parallel to upper surface 86, or at any other angle that enables insert 14 to function as described herein). In the exemplary embodiment, the retainer elements 98 are substantially rectangular in cross-section and are configured to frictionally engage the side edges 22 and 24 of the test elements 16 to facilitate retaining the test elements 16 within the interior space 76 of the insert 14, while providing relatively unrestricted access to the test elements 16. In the exemplary embodiment, the retainer elements 98 are fabricated from a resilient material (e.g., an elastomeric material such as Santoprene®, which is commercially available from ExxonMobil; Irving, Tex. USA). Alternatively, retainer elements 98 may be fabricated from any other elastomeric or resilient material that enables insert 14 to function as described herein.

In the exemplary embodiment, the main body 70 includes at least a pair of securing tabs 102 extending outwardly from an outer surface 104 of the sidewall 84. The securing tabs 102 extend outward in a direction of the minor transverse axis T4 and extend laterally along the outer surface 104 of the sidewall 84 in a direction of the major transverse axis T3 for engagement with an inner surface 106 of the housing 12 to aid in retaining the insert 14 within the interior space 36 of the housing 12. Alternatively, the main body 70 may include any number of securing tabs 102 that enable insert 14 to function as described herein. In some instances, the securing tabs 102 are substantially centered on the main body 70 between the front portion 90 and the rear portion 92 and extend laterally in a range between about 25% and about 75% of distance between the front portion 90 and the rear portion 92. In some instances, the range can be between about 30% and about 70%, between about 35% and about 65%, between about 40% to about 60%, between about 45% and about 55%, or about 50%. Alternatively, the range can be from about 25% to about 30%, from about 30% to about 35%, from about 35% to about 40%, from about 40% to about 45%, from about 45% to about 50%, from about 50% to about 55%, from about 55% to about 60%, from about 60% to about 65%, from about 65% to about 70%, or from about 70% to about 75%. In other instances, the securing tabs 102 may extend laterally any length that enables insert 14 to function as described herein.

The securing tabs 102 are formed substantially parallel to the bottom wall 78. However, it is understood that the securing tabs 102 can be formed at an angle relative to the bottom wall 78 such as, for example, securing tabs 102 can be formed substantially parallel to upper surface 86, or at any other angle that enables insert 14 to function as described herein. In the exemplary embodiment, the securing tabs 102 are substantially rectangular in cross-section and are configured to frictionally engage the inner surface 106 of the housing 12 to facilitate retaining the insert 14 securely within the interior space 36 of the housing 12, while providing relatively unrestricted access to the insert 14 for removal of the insert 14 from the housing 12. In the exemplary embodiment, the securing tabs 102 are fabricated from a resilient, elastomeric material such as, for example, SANTOPRENE®. Alternatively, securing tabs 102 may be fabricated from any other elastomeric or resilient material that enables insert 14 to function as described herein.

Figure 9:
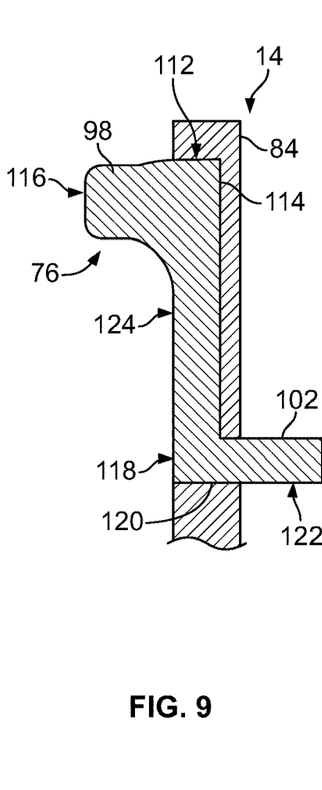
FIG. 9 is an enlarged cross sectional view of a retainer element and securing tabs that can be used with the insert shown in FIG. 4.

FIG. 9 is an enlarged cross sectional view of one of the retainer elements 98 and the securing tabs 102 used with the insert 14 shown in FIG. 4. In the exemplary embodiment, the retainer elements 98 each include a mounting portion 112 coupled within a corresponding lateral groove 114 formed in the sidewall 84 of the main body 70 (see, FIG. 4), with the tip or end portion 116 extending into the interior space 76 of the main body 70 for frictional engagement with a corresponding one of the side edges 22 and 24 of the test elements 16 (see, FIG. 2). The distance separating the tip portions 116 of the retainer elements 98 or an angle at which the retainer elements 98 extend into the interior space 76 of the main body 70 may be adjusted to accommodate test elements 16 having different widths Ws. Such adjustment of the distance separating the tip portions 116 of the retainer elements 98 or the angular orientation of the retainer elements 98 may be accomplished by varying the position or angular orientation of the retainer elements 98 relative to the insert 14. Alternatively, retainer elements 98 may be removed and replaced with retainer elements having a different configuration defining a different separation distance or angular orientation relative to the insert 14.

Further, the securing tabs 102 each include a mounting portion 118 coupled within a corresponding lateral groove 120 formed in the sidewall 84 of the main body 70 (see, FIG. 4), with the tip or end portion 122 extending outward, away from the interior space 76 of the main body 70 for frictional engagement with the inner surface 106 of the housing 12 (see, FIG. 3). The distance separating the tip portions 116 of the securing tabs 102 or an angle at which the securing tabs 102 extend into the interior region 36 of the housing 12 may be adjusted to accommodate housing 12 having different sizes. Such adjustment of the distance separating the tip portions 122 of the securing tabs 102 or the angular orientation of the securing tabs 102 may be accomplished by varying the position or angular orientation of the securing tabs 102 relative to the insert 14. Alternatively, securing tabs 102 may be removed and replaced with securing tabs having a different configuration defining a different separation distance or angular orientation relative to the insert 14.

In the exemplary embodiment, retainer elements 98 and securing tabs 102 may be formed integrally, having a connecting portion 124 formed in a medial groove 126 extending substantially upwardly from lateral groove 120 to lateral groove 114 (see, FIG. 7). Alternatively, the medial groove 126 may be omitted from the insert 14 so that retainer elements 98 and securing tabs 102 are formed independent of each other.

In the exemplary embodiment, the retainer elements 98 and securing tabs 102 may be coupled to the main body 70 by a two-shot injection molding process. Alternatively, the retainer elements 98 and securing tabs 102 may be coupled to the main body 70 by mechanical fastening, pinning, fusing, welding, adhesive bonding, or other suitable attachment techniques. In some instances, retainer elements 98 and securing tabs 102 may be configured to be adjustable relative to the insert 14 (e.g., adjustable in position or orientation), or configured for disengagement and removal from the insert 14 for replacement by a different configuration of the retainer elements 98 and securing tabs 102 to accommodate the test elements 16 having different nominal widths Ws and the housing 12 having different sizes. Although a specific configuration of the retainer elements 98 and the securing tabs 102 have been described, it should be understood that other configurations of the retainer elements 98 and securing tabs 102, and other suitable techniques for attaching the retainer elements 98 and securing tabs 102 to the insert 14 are also contemplated as falling within the scope of the present disclosure.

Referring back to FIGS. 4 and 5, the main body 70 of the insert 14 includes at least one lateral vent 128 formed through the sidewall 84 of the insert 14 to enable air to pass from the interior space 76 of the insert 14 to the interior space 36 of the housing. In the exemplary embodiment, the insert 14 includes a pair of lateral vents 128 formed in the first side portion 94 symmetrical about longitudinal axis L, and a symmetrical pair of lateral vents formed in the second side portion 96 of the insert 14. Each one of the lateral vents 128 are rectangular in shape and are formed substantially parallel to bottom wall 78 of the insert 14, spaced upward from the floor panel 110.

In the exemplary embodiment, the insert 14 is a molded component that is fabricated from two separate materials including a polymeric or plastic material including, for example, polypropylene or polyethylene, and an elastomeric material such as, for example, Santoprene®. Accordingly, the features of the insert 14 described herein may have a draft angle associated with each wall and/or cavity to promote removal of the insert 14 from a mold. The component 14 is fabricated by a two-shot injection molding process. Alternatively, the insert 14 may be fabricated by methods other than molding (e.g., machining) and therefore may not have a draft angle associated with the features as described herein. In the exemplary embodiment, to facilitate injection molding, the insert 14 is fabricated so that the first side portion 94 and the second side portion 96 are substantially symmetrical and separated from each other about a parting line falling on a plane coincident with the longitudinal axis L and substantially parallel to the side view plane of FIG. 5. As described above, the insert 14 may include features and/or elements that are not symmetrical with respect to each other.

Figure 10:
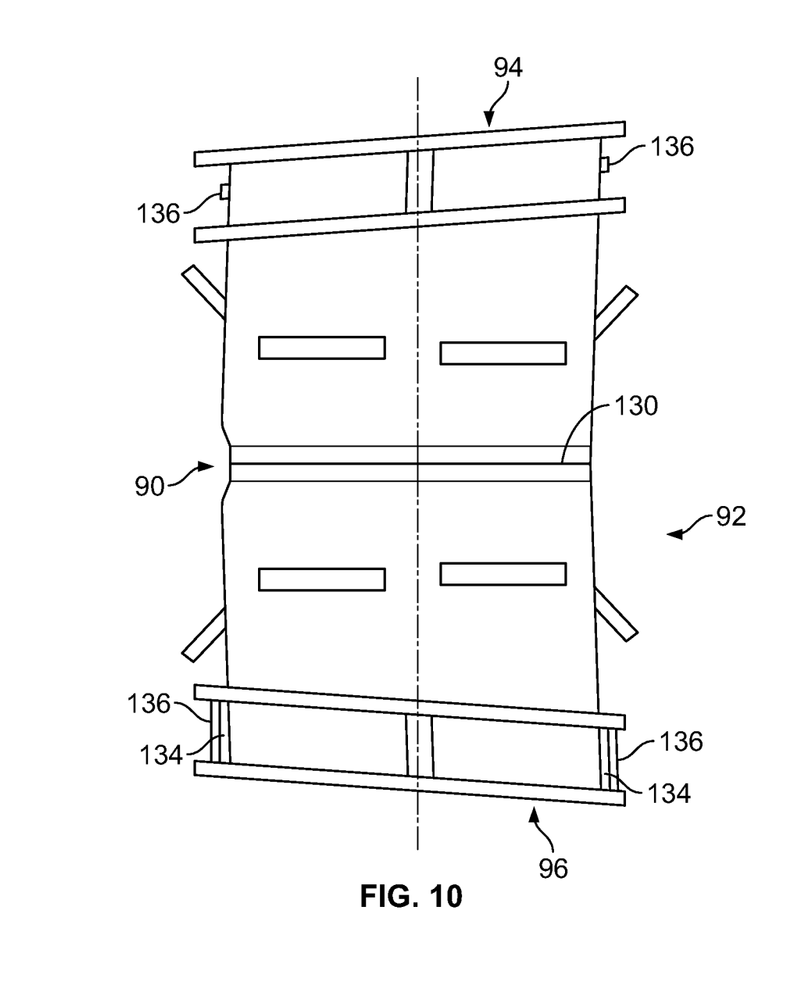
FIG. 10 is a plan view of the insert shown in FIG. 4, illustrating the insert rotated about a hinge to a substantially flat position.

In one suitable embodiment, the first side portion 94 and the second side portion 96 are hinged together for hinged motion relative therebetween. More specifically, the first side portion 94 and the second side portion 96 are hinged to each other in the manner of a "living hinge" 130 in which the first side portion 94 is formed integrally with the second side portion 96 along a thinned or scored connecting web that is sufficiently flexible to allow hinged motion of the first side portion 94 relative to the second side portion 96. It is understood, though, that the first side portion 94 may be formed separate from the second side portion 96 and mechanically hinged thereto by a suitable hinge mechanism (not shown) without departing from the scope of this present disclosure. Furthermore, the first side portion 94 may be formed separate from the second side portion 96 and configured to snap or join together with suitable locking mechanisms (not shown) without departing from the scope of this present disclosure.

FIG. 10 is a plan view of one suitable embodiment of the insert 14 in an open position, such that the first side portion 94 and the second side portion 96 are rotated about hinge 130 to a substantially flat position (i.e., the first side portion is rotated about 180 degrees about hinge 130 relative to the second side portion 96). With particular reference to FIGS. 4, 6 and 10, the insert 14 includes at least one locking mechanism 132. In the exemplary embodiment, the insert 14 includes a pair of locking mechanisms 132, one positioned at the front portion 90 and one positioned at the rear portion 92 of the insert 14, between the upper surface 86 and the lip 108. The locking mechanisms 132 are substantially the same, and for clarity, only one will be described below.

Each locking mechanism 132 is configured to secure the first side portion 94 to second side portion 96 when respective side portions are rotated about hinge 130 into face-to-face contact. The locking mechanism 132 includes a generally rectangular opening 134 formed by a catch member 136 extending between the upper surface 86 and the lip 108, and spaced away from the outer surface 104 of the sidewall 84 on second side portion 96. In addition, the locking mechanism 132 includes resilient, upstanding members 138 terminating in a latch portion 140 (broadly, "latch member"). The upstanding members 138 are biased slightly outward and extend toward second side portion 96 when in the closed position shown, for example, in FIG. 6, for latching engagement with catch member 136. In the exemplary embodiment, the upstanding members extend through opening 134, and the latch 140 latching engages with catch member 136 to releasably secure the first side portion 94 to the second side portion 96 of the insert 14.

With reference to FIGS. 4-6, the insert 14 includes a pair of resilient retention arms 142 that extend outward and upward from the front portion 90 and the rear portion 92 of the main body 70. The retention arms 142 extend outward beyond a periphery of the upper surface 86 and are configured to engage inner surface 106 of the housing 12 to aid in retaining the insert 14 within the interior space 36 of the housing 12. Further, the insert 14 includes a plurality of retention lugs 144 extending outward from the first side portion 94 and the second side portion 96 in a direction of the minor transverse axis T4. The first side portion includes a first pair of retention lugs 144 position at the lower end portion 72 and the second side portion 96 includes an opposite pair of retention lugs 144 symmetrical to the first pair. The retention lugs 144 are configured to engage an inner portion of the housing 12 to aid in positioning and retaining the insert 14 within the interior space 36 of the housing 12. It is contemplated that the retention arms 142 and the retention lugs 144 can be omitted from the insert 14.

Figure 11:
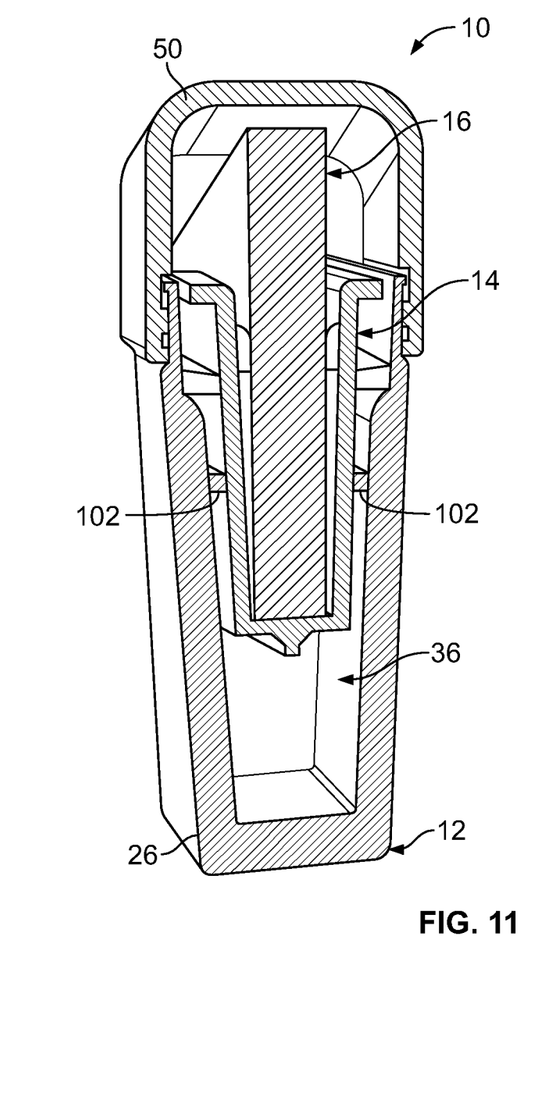
FIG. 11 is a cross sectional view of the storage container shown in FIG. 1, in a closed position, taken along line 11-11 in FIG. 1.

FIG. 11 is a cross sectional view of the storage container 10, in the closed position, taken along line 11-11 shown in FIG. 1. In the exemplary embodiment, the insert 14 is positioned within the interior space 36 of the body 26 of the housing 12, and is configured to retain a plurality of the test elements 16 therein. As indicated above with reference to FIGS. 4-6, the main body 70 of the insert 14 includes one or more securing tabs 102 extending outwardly from the outer surface 104 of the sidewall 84 in the direction of the second transverse axis T2 for frictional engagement with the inner surface 106 or the desiccant 13 of the body 26 of the housing 12 to facilitate retaining the insert 14 within the inner space 36 of the housing. In addition, the securing tabs 102 facilitate stability of the insert component 14 within the housing 12. The lip 108 of the insert 14 engages an upper edge of the desiccant 13 to facilitate positioning the insert 14 vertically within the interior space 36 of the housing 12.

In use, a user opens the cap 50 as shown in FIG. 1, and removes one of the test elements 16. The user may then close the cap 50 to retain the remaining test elements 16 within the storage container 10. Air that enters the inner space of the storage container 10 is permitted to circulate through the storage container 10 by passing into the interior space 76 of the insert 14 through the space vacated by the test strip 16 removed by the user. The air can circulate through the interior space 76 of the insert and the interior space 36 of the housing 12 by passing through the lateral vents 128. This circulation of the air enables the desiccant 13 to remove excess humidity or moisture from the air to facilitate maintaining the integrity of the test elements 16.

Figure 12:
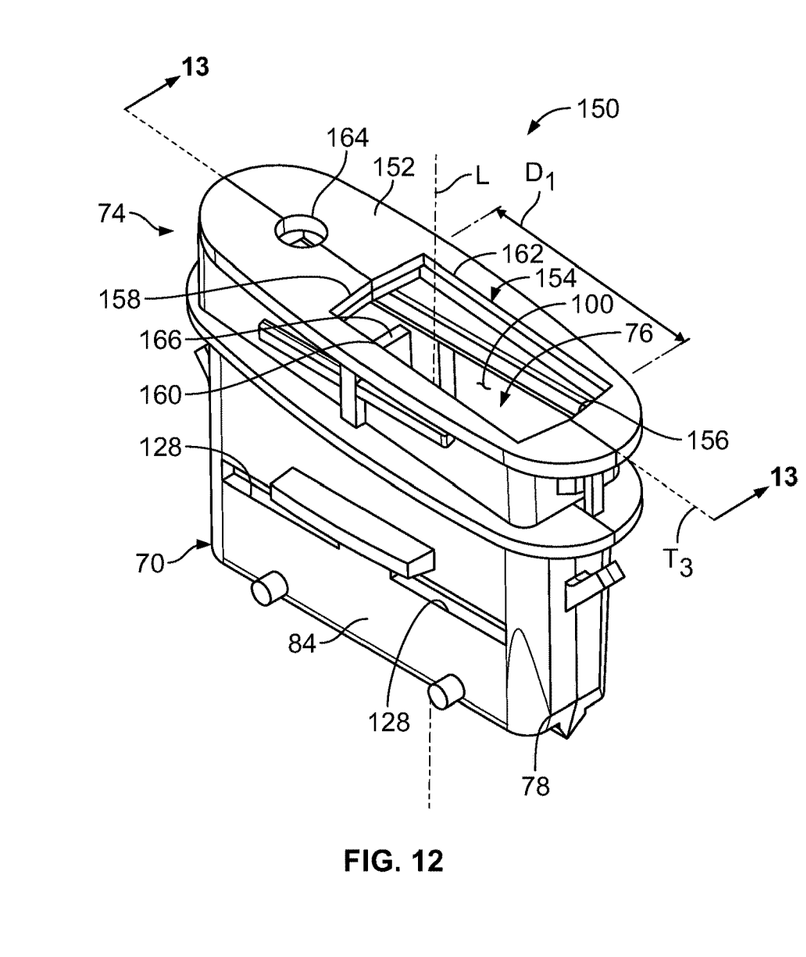
FIG. 12 is a perspective view of an alternative insert that can be used with the storage container shown in FIG. 1.
Figure 13:
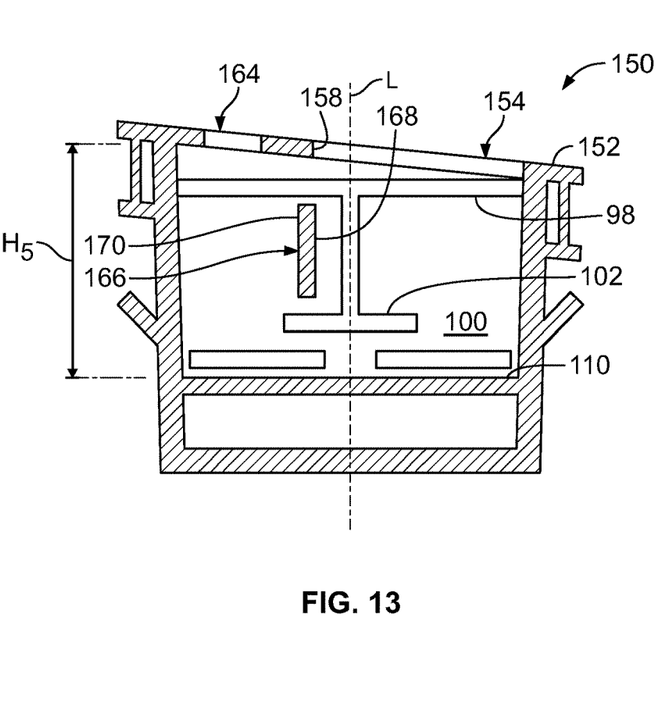
FIG. 13 is a cross sectional view of the insert shown in FIG. 12, taken along line 13-13 in FIG. 12.

FIG. 12 is a perspective view of an alternative insert 150 that can be used with the storage container 10 shown in FIG. 1. FIG. 13 is a cross sectional view of the insert 150, taken along line 13-13 shown in FIG. 12. As shown in FIGS. 12 and 13, the insert 150 is substantially the same as the insert 14 described in FIGS. 4-10; however, the differences will be describe below.

With reference to FIGS. 12 and 13, the insert 150 is configured for interchangeable engagement with the housing 12. The insert 150 includes the main body 70 having the interior space 76 configured to receive and retain the test elements 16 (see, FIG. 1) therein. The main body 70 also includes the tubular sidewall 84 that extends substantially axially along the longitudinal axis L from the bottom wall 78 toward the upper end portion 74, terminating at a top or upper surface 152. The bottom wall 78 and the tubular sidewall 84 together define a tubular configuration having the interior space 76 and an upper opening 154 at the upper surface 152.

In one suitable embodiment, the upper opening 154 is substantially rectangular in shape. Alternatively, the upper opening 154 can have any shape that enables the insert 150 to function as described herein. In the embodiment shown in FIG. 12, the upper opening 154 has a front edge portion 156 and an opposite rear edge portion 158. Extending between the front edge portion 156 and the rear edge portion 158 is a first side edge portion 160 and an opposite second side edge portion 162. In the exemplary embodiment, the front edge portion 156 is generally aligned with inner surface 100 of the tubular sidewall 84. Furthermore, each one of the first side edge portion 160 and the second side edge portion 162 is generally aligned with the inner surface 100 of the tubular sidewall 84. The rear edge portion 158 is substantially parallel to and offset from the front edge portion 156 a predefined distance D1. The predefined distance D1 can be sized such that the upper opening 154 can accommodate and securely retain a predefined number of test elements 16.

For example, the predefined distance D1 can be adjusted such that the insert 150 can accommodate between about 5 test elements to about 50 test elements, between about 10 test elements to about 45 test elements, between about 15 test elements to about 40 test elements, between about 20 test elements to about 35 test elements, or between about 25 test elements to about 30 test elements. Alternatively, the insert can accommodate from about 5 test elements to about 10 test elements, from about 10 test elements to about 15 test elements, from about 15 test elements to about 20 test elements, from about 20 test elements to about 25 test elements, from about 25 test elements to about 30 test elements, from about 30 test elements to about 35 test elements, from about 35 test elements to about 40 test elements, from about 40 test elements to about 45 test elements, or from about 45 test elements 50 test elements. Alternatively still, the insert can accommodate about 5 test elements, about 10 test elements, about 15 test elements, about 20 test elements, about 25 test elements, about 30 test elements, about 35 test elements, about 40 test elements, about 45 test elements, about 50 test elements or more.

As seen in FIG. 12, the insert 150 includes a vent hole 164 formed through the upper surface 152 adjacent the upper opening 154. As shown, the vent hole 164 is formed substantially centered on the major transverse axis T3. Alternatively, the vent hole 164 may be formed in any portion of the upper surface 152 that enables to vent hole 164 to function as described herein. In some instances, more than one vent hole 164 may be formed through the upper surface 152 for increased air circulation within the insert 150. The vent hole 164 is configured to enable air to circulate through the interior space 76 of the insert 150 in combination with the lateral vents 128 to enable the interior space 76 to reach a dry equilibrium soon after closure of the storage container 10. In the exemplary embodiment, the vent hole 164 is circular. Alternatively, the vent hole 164 may be formed in other shapes including, but not limited to, a square, a rectangular slit, etc. It also is contemplated that the vent hole 164 may be omitted from the insert 150.

Referring to FIG. 13, the main body 70 of the insert 150 includes an upward extending support wall 166 that projects from the inner surface 100 of the tubular sidewall 84 into the interior space 76. The support wall 166 has a front surface 168 and a rear surface 170. The support wall 166 extends in the direction of the longitudinal axis L between retainer element 98 and securing tab 102, having its front surface 168 substantially vertically aligned with the rear edge portion 158 of the upper opening 154. In one suitable embodiment, the support wall 166 is offset from the floor panel 110 and may be positioned at various elevations within the interior space 76. In addition, the support wall 166 extends along less than the maximum height dimension H5 of the interior space 76. Alternatively, in other suitable embodiments, the support wall 166 may extend substantially entirely along the entire height dimension H5 of the interior space 76. The support wall 166 is configured for engagement with the test elements 16 to facilitate maintaining the test elements 16 in a substantially upright orientation within the interior space 76 of the insert 150 generally parallel with the longitudinal axis L, and preventing the test elements 16 from sliding into the interior space 76 of the insert 150 when only a few of the test elements remain in the insert. It is contemplated that the support wall 166 can be omitted from the insert 150.

In operation, the test elements 16 are positioned within the interior space 76 of the insert 150 where they are maintained in a substantially vertical orientation by the support wall 166 to prevent the test elements 16 from falling lengthwise into the interior space 76 as the number of test elements 16 is gradually decreased through use. Because the support wall 166 extends along less than the entire height dimension H5 of the interior space 76, the support wall 166 does not impede removal of the test elements 16 from the interior space 76 of the insert 150. The support wall 166 functions as a stabilizer to maintain the test elements 16 in a substantially upright orientation and in a well-ordered arrangement within the insert 150 for presentation to the user, while facilitating relatively easy access and removal of an individual test strip 16 from the insert 150.

Exemplary embodiments of interchangeable inserts for a storage container are described above in detail. The apparatus and systems are not limited to the specific embodiments described herein, but rather, operations of the methods and components of the systems may be utilized independently and separately from other operations or components described herein. For example, the systems and apparatus described herein may have other industrial or consumer applications and are not limited to practice with biosensor components as described herein. Rather, one or more embodiments may be implemented and utilized in connection with other industries.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims. Numbered embodiments are presented below.

1. An insert for a storage container configured to receive a plurality of vertically oriented items, the insert comprising:
   a body comprising a base, an upper surface having an upper opening, and an upstanding tubular sidewall extending between said base and said upper surface, the base and the upstanding tubular sidewall together defining an interior space, wherein the upstanding tubular sidewall comprising an inner surface and an outer surface;
   a pair of resilient securing tabs extending laterally from the outer surface of the upstanding tubular sidewall, wherein the pair of resilient securing tabs frictionally engages the storage container for releasably coupling the insert to the storage container; and
   a first vent opening extending through the upstanding tubular sidewall through which air can enter the interior space of the body.

2. The insert of Embodiment 1, wherein the securing tabs of the pair of resilient securing tabs are oppositely oriented.

3. The insert of Embodiments 1 or 2 further comprising a pair of resilient retainer elements extending laterally from the inner surface of the upstanding tubular sidewall and inwardly into the interior space, wherein the pair of resilient retainer elements frictionally engages the vertically oriented items to facilitate retaining the vertically oriented items within the interior space.

4. The insert of Embodiment 3, wherein the retainer elements of the pair of resilient retainer elements are oppositely oriented.

5. The insert of Embodiments 1 to 4, wherein the first vent opening comprises a pair of first vent openings oppositely oriented to one another.

6. The insert of Embodiments 1 to 5, wherein the upper surface comprises an annular flange extending outward from the upstanding tubular sidewall, the annular flange comprising a substantially elliptically shaped periphery.

7. The insert of Embodiment 6 further comprising a lip coupled to the outer surface of the upstanding tubular sidewall, the lip spaced away from the upper surface and comprising a substantially elliptically shaped periphery corresponding to the upper surface.

8. The insert of Embodiments 1 to 7, wherein the upper surface comprises a second vent opening extending through the upper surface through which air can enter the interior space of the body.

9. The insert of Embodiments 1 to 8, wherein at least a portion of an edge defining the upper opening is coterminous with the inner surface of the upstanding tubular sidewall.

10. The insert of Embodiment 9, wherein the entirety of the edge is coterminous with the inner surface of the upstanding tubular sidewall.

11. The insert of Embodiment 9, wherein the body comprises a front portion, a rear portion, and transversely opposite side portions, and wherein the edge comprises a rear portion spaced inwardly away from the rear portion of the body.

12. The insert of Embodiment 11 further comprising a support wall having a front surface and a rear surface, the support wall extending inwardly from the inner surface of the upstanding tubular sidewall into the interior space, and extending upwardly between the base and the upper surface.

13. The insert of Embodiment 12, wherein the front surface of the support wall is substantially vertically aligned with the edge rear portion of the upper opening.

14. The insert of Embodiment 12, wherein a lower end of the support wall is offset from the base and an upper end of the support wall is offset from the upper surface.

15. The insert of Embodiments 1 to 14 further comprising a floor panel disposed within the interior space and spaced away from the base.

16. An insert as substantially described and shown herein.

17. An insert for a storage container configured to receive a plurality of vertically oriented items, the insert comprising:
a first side portion and a second side portion hingedly coupled together, each of the first side portion and the second side portion comprising a base, an upper surface, an upstanding tubular sidewall extending between the base and the upper surface, the upstanding tubular sidewall comprising an inner surface and an outer surface and a resilient securing tab extending from the outer surface, each of the first side portion and the second side portion further comprising a lip coupled to the outer surface of the upstanding tubular sidewall, the lip being spaced away from the upper surface, the first side portion and the second side portion being moveable between a closed configuration, where the first side portion and the second side portion are in face-to-face contact, and an open configuration, wherein the first side portion and the second side portion are rotated apart;
a catch member coupled to one of the first side portion and the second side portion, the catch member extending between the upper surface and the lip and defining a catch opening;
a latch member coupled to the outer surface of the tubular sidewall of the other one of the first side portion and the second side portion wherein the latch member extends through the catch opening and engages the catch member; and
a living hinge coupled between the first side portion and the second side portion to enable the first side portion and the second side portion to be rotated into face-to-face contact.

18. The insert of Embodiment 17, wherein the latch member comprises a resilient, upstanding member and a latch portion, the latch portion configured to engage the catch member.

19. The insert of Embodiments 17 or 18 further comprising a pair of resilient retention arms configured to facilitate retaining the insert within the storage container when the insert is in a closed configuration.

20. The insert of Embodiments 17 to 19 further comprising a pair of retention lugs configured to engage an inner portion of the storage container to facilitate positioning and retaining the insert within the storage container when the insert is in a closed configuration.

21. The insert of Embodiments 17 to 20 further comprising a first catch member and a second catch member.

The invention claimed is:

1. An insert for a storage container configured to receive a plurality of vertically oriented items, the insert comprising:
a first side portion and a second side portion hingedly coupled together, each of the first side portion and the second side portion comprising a base, an upper surface, an upstanding tubular sidewall extending between the base and the upper surface, the upstanding tubular sidewall comprising an inner surface and an outer surface and a resilient securing tab extending outwardly from the outer surface, each of the first side portion and the second side portion further comprising a lip coupled to the outer surface of the upstanding tubular sidewall, the lip being spaced away from the upper surface, the first side portion and the second side portion being moveable between a closed configuration, where the first side portion and the second side portion are in face-to-face contact, and an open configuration, wherein the first side portion and the second side portion are rotated apart;
at least one catch member coupled to one of the first side portion and the second side portion, the at least one catch member extending between the upper surface and the lip and defining a catch opening;
a latch member coupled to the outer surface of the tubular sidewall of the other one of the first side portion and the second side portion wherein the latch member extends through the catch opening and engages the at least one catch member; and
a living hinge coupled between the first side portion and the second side portion to enable the first side portion and the second side portion to be rotated into face-to-face contact.

2. The insert of claim 1, wherein the latch member comprises a resilient, upstanding member and a latch portion, the latch portion configured to engage the at least one catch member.

3. The insert of claim 1 further comprising a pair of resilient retention arms configured to facilitate retaining the insert within the storage container when the insert is in a closed configuration.

4. The insert of claim 1 further comprising a pair of retention lugs configured to engage an inner portion of the storage container to facilitate positioning and retaining the insert within the storage container when the insert is in a closed configuration.

5. The insert of claim 1, wherein the at least one catch member comprises a first catch member and a second catch member.

6. An insert for a storage container configured to receive a plurality of vertically oriented items, the insert comprising:
a first side portion and a second side portion hingedly coupled to the first side portion, each of the first side portion and the second side portion comprising a base, an upper surface, a tubular sidewall extending between the base and the upper surface, a lip extending outwardly from the tubular sidewall adjacent the upper surface, and a resilient securing tab extending outwardly from the tubular sidewall for releasably coupling the insert to the storage container, the resilient securing tab spaced from the lip, the first side portion and the second side portion being moveable between a closed configuration, wherein the first side portion and the second side portion are in face-to-face contact, and an open configuration, wherein the first side portion and the second side portion are rotated apart;

a catch member coupled to one of the first side portion and the second side portion, the catch member extending between the upper surface and the lip and defining a catch opening;

a latch member coupled to the other one of the first side portion and the second side portion, the latch member extending through the catch opening and engaging the catch member; and a living hinge coupled between the first side portion and the second side portion to enable the first side portion and the second side portion to be rotated into face-to-face contact.

7. The insert of claim 6, wherein the latch member comprises a resilient, upstanding member and a latch portion, the latch portion configured to engage the catch member.

8. The insert of claim 6 further comprising a pair of resilient retention arms configured to facilitate retaining the insert within the storage container when the insert is in a closed configuration.

9. The insert of claim 6 further comprising a pair of retention lugs configured to engage an inner portion of the storage container to facilitate positioning and retaining the insert within the storage container when the insert is in a closed configuration.

* * * * *